United States Patent [19]

Kameswaran et al.

[11] Patent Number: 5,151,536
[45] Date of Patent: Sep. 29, 1992

[54] PROCESS FOR THE MANUFACTURE OF PESTICIDAL 1-(ALKOXYMETHYL) PYRROLE COMPOUNDS

[75] Inventors: Venkataraman Kameswaran, Princeton Junction; Jerry M. Barton, East Windsor, both of N.J.

[73] Assignee: American Cyanamid Company, Stamford, Conn.

[21] Appl. No.: 628,744

[22] Filed: Dec. 17, 1990

[51] Int. Cl.$^5$ ............... C07D 207/30; C07D 207/12; C07D 207/30; C07D 207/18
[52] U.S. Cl. ................... 548/530; 548/531; 548/550; 548/562; 548/566
[58] Field of Search ............... 548/562, 566, 531, 530, 548/550

[56] References Cited

PUBLICATIONS

CA 111:194576w Preparation of Arylpyrrole Pesticides Brown et al. p. 755, Jul. 1987.
CA 111:111037x Preparation of Arylpyrrole Molluscicides, Herman et al. p. 271, Oct. 1987.
CA 113:115076y Preparation of Phenylpyrrole Derivatives and Method of Controlling Pathogenic Fungi, Froyd et al. p. 671, Aug. 1988.
CA 113:231205p Preparation of Pyrrolecarbonitrile... Molluscicidal Agents, Brown et al., p. 706, Dec. 1988.

*Primary Examiner*—Mary C. Lee
*Assistant Examiner*—Joseph K. McKane
*Attorney, Agent, or Firm*—Alice C. Brennan

[57] ABSTRACT

There is provided a single step procedure for the manufacture of 1-(alkoxymethyl)pyrrole compounds by reacting the appropriate pyrrole precursor with a dihalomethane reagent in the presence of an alkali metal alkoxide. The 1-(alkoxymethyl)pyrrole compounds are useful as molluscicidal, insecticidal, acaricidal and nematocidal agents.

10 Claims, No Drawings

PROCESS FOR THE MANUFACTURE OF PESTICIDAL 1-(ALKOXYMETHYL) PYRROLE COMPOUNDS

BACKGROUND OF THE INVENTION

Pyrrole carbonitrile, nitropyrrole, arylpyrrole and diarylpyrrole compounds and derivatives thereof are highly effective molluscicidal, insecticidal, acaricidal and nematocidal agents. In general, pyrrole carbonitrile, nitropyrrole, arylpyrrole and diarylpyrrole derivatives containing an alkoxymethyl substituent on the pyrrole nitrogen atom are more efficacious than the parent pyrrole compound.

A process for the preparation of insecticidal 1-(alkoxymethyl)-2-aryl-4-halopyrrole compounds is described in copending U.S. application Ser. No. 634,288, filed on Dec. 26, 1990. However, this process is limited to the preparation of certain insecticidal pyrroles containing aryl, halo and trifluoromethyl substituents in the 2, 4 and 5 positions on the pyrrole ring, respectively.

It is an object of this invention to provide a simple, single step procedure for the manufacture of 1-alkoxymethyl derivatives of a wide variety of important pesticidal pyrrole compounds.

SUMMARY OF THE INVENTION

The present invention is directed to a process for the preparation of pyrrole compounds of formula I wherein
R is $C_1-C_6$ alkyl;
W is CN or $NO_2$;
X is H, CN, halogen or phenyl optionally substituted with one to three halogens, CN, $NO_2$, $C_1-C_3$ alkyl, $C_1-C_3$ alkoxy, $C_1-C_3$ alkylthio, $C_1-C_3$ alkylsulfinyl, $C_1-C_3$ alkylsulfonyl, $CF_3$, $R_1CF_2R_2$, $R_3CO$ or $NR_4R_5$ groups;
Y is $CF_3$ or halogen;
Z is H, $CF_3$, halogen or phenyl optionally substituted with one to three halogen, CN, $NO_2$, $C_1-C_3$ alkyl, $C_1-C_3$ alkoxy, $C_1-C_3$ alkylthio, $C_1-C_3$ alkylsulfinyl, $C_1-C_3$ alkylsulfonyl, $CF_3$, $R_1CF_2R_2$, $R_3CO$ or $NR_4R_5$ groups;
$R_1$ is H, F, $CHF_2$, $CHFCl$ or $CF_3$;
$R_2$ is $S(O)_n$ or O;
$R_3$ is $C_1-C_3$ alkyl, $C_1-C_3$ alkoxy or $NR_4R_5$;
$R_4$ is H or $C_1-C_3$ alkyl;
$R_5$ is H, $C_1-C_3$ alkyl or $R_6CO$;
$R_6$ is H or $C_1-C_3$ alkyl and
n is an integer of 0, 1 or 2 which comprises reacting a compound of formula II wherein W, X, Y and Z are described above with at least one molar equivalent of a dihalomethane in the presence of at least two molar equivalents of an alkali metal $C_1-C_6$alkoxide and optionally about one molar equivalent of an alkali metal hydride and a solvent.

The compounds of formula II and methods of preparation thereof are described in copending U.S. applications Ser. No. 392,495, filed on Aug. 11, 1989, Ser. No. 430,601, filed on Nov. 6, 1989, and Ser. No. 621,162, filed on Nov. 30, 1990, which are incorporated herein by reference thereto.

DESCRIPTION OF THE INVENTION

Surprisingly, it has been found that the 1-alkoxymethyl derivativization of a practically unlimited number of pyrrole precursors may be achieved efficiently and effectively in a simple, one step procedure. The procedure avoids the use, preparation and handling of environmentally unsafe intermediates such as chloromethyl ethyl ether. Advantageously, the pyrrole compounds of formula I may be prepared by reacting a suitable pyrrole compound of formula II with at least one molar equivalent of a dihalomethane reagent in the presence of an alkali metal alkoxide and optionally an alkali metal hydride and a solvent at preferably an elevated temperature. The process is illustrated in Flow Diagram I.

FLOW DIAGRAM I

In the above flow diagram, R, W, X, Y and Z are as described hereinabove, M is an alkali metal such as sodium, potassium lithium and the like, preferably sodium, and X' and X" are each independently chlorine, bromine or iodine.

The solvents suitable for use in the process of the present invention include ethers such as dioxane, tetrahydrofuran, ethylene glycol, diethoxymethane, dimethyl ether and the like. A preferred solvent is tetrahydrofuran. Alkali metal alkoxides useful in the process include sodium methoxide, sodium ethoxide, potassium t-butoxide and so forth. Reaction temperatures greater than 30° C. are preferred. The formula I products may be isolated using standard procedures such as concentration and extraction or filtration.

Among the compounds that may be prepared by the method of the present invention are those shown in Table I.

TABLE I

| W | X | Y | Z | R | MP °C. |
|---|---|---|---|---|---|
| 3-CN | 4-Cl | 5-Cl | 2-(p-CF$_3$O—C$_6$H$_5$) | C$_2$H$_5$ | 46-47 |
| 4-NO$_2$ | 2-Br | 3-Br | 5-(p-Cl—C$_6$H$_5$) | C$_2$H$_5$ | — |
| 4-NO$_2$ | 2-Cl | 3-Cl | 5-(3,4-diCl—C$_6$H$_5$) | C$_2$H$_5$ | 118-120 |
| 4-NO$_2$ | 2-Cl | 3-Cl | 5-(p-Br—C$_6$H$_5$) | C$_2$H$_5$ | 115-117 |
| 3-CN | 4-Cl | 5-Cl | 2-(p-CF$_3$—C$_6$H$_5$) | C$_2$H$_5$ | 99-100 |
| 3-CN | 4-Cl | 5-Cl | 2-(3,4-diCl—C$_6$H$_5$) | C$_2$H$_5$ | 126-130 |
| 3-CN | 4-Cl | 5-Cl | 2-(p-Cl—C$_6$H$_5$) | C$_2$H$_5$ | 108-111 |
| 4-NO$_2$ | 2-(p-Cl—C$_6$H$_5$) | 5-CF$_3$ | 3-(p-Cl—C$_6$H$_5$) | C$_2$H$_5$ | — |
| 3-CN | 4-Br | 5-Br | 2-Br | C$_2$H$_5$ | 139-143 |
| 3-CN | 4-Br | 5-CF$_3$ | 2-(p-Cl—C$_6$H$_5$) | C$_2$H$_5$ | 91-92 |
| 3-CN | 4-Cl | 5-CF$_3$ | 2-(p-Cl—C$_6$H$_5$) | C$_2$H$_5$ | 100-103 |
| 4-NO$_2$ | 3-(p-Cl—C$_6$H$_5$) | 5-CF$_3$ | 2-(p-Cl—C$_6$H$_5$) | C$_2$H$_5$ | — |
| 3-NO$_2$ | 4-(3,4-diCl—C$_6$H$_5$) | 5-CF$_3$ | 2-(p-Cl—C$_6$H$_5$) | C$_2$H$_5$ | 121-123 |
| 4-NO$_2$ | 3-(m-CN—C$_6$H$_5$) | 2-CF$_3$ | 5-(p-ClC$_6$H$_5$) | C$_2$H$_5$ | — |
| 3-CN | 4-Br | 5-Br | 2-(p-CF$_3$—C$_6$H$_5$) | C$_2$H$_5$ | 114-116 |
| 3-CN | 2-Cl | 4-Cl | 5-(3,4-diCl—C$_6$H$_5$) | C$_2$H$_5$ | 106-109 |
| 3-CN | 2-Cl | 4-Br | 5-(p-Br—C$_6$H$_5$) | C$_2$H$_5$ | 104-106 |

In order to facilitate a further understanding of the present invention, the following examples are presented to illustrate more specific details thereof. The invention is not to be limited thereby except as defined in the claims. The term glc designates gas-liquid chromatography and the term HPLC designates high pressure liquid chromatography. Unless otherwise noted, all parts are by weight.

EXAMPLE 1

Preparation of
4-Bromo-2-(p-chlorophenyl)-1-ethoxymethyl)-5-(trifluoromethyl)pyrrole-3-carbonitrile

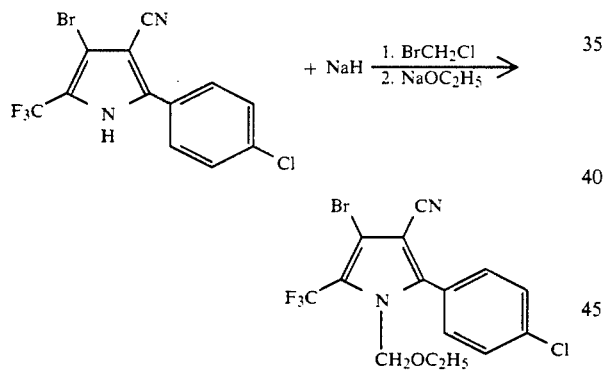

A mixture of a 60% mineral oil dispersion of NaH (2.0 g, 0.03 mol NaH) in tetrahydrofuran under N$_2$ is treated dropwise with a solution of 4-bromo-2-(p-chlorophenyl)-5-(trifluoromethyl)pyrrole-3-carbonitrile 10.5 g, 0.03 mol) in tetrahydrofuran at 20°-30° C., stirred for 15 minutes at 15° C. to 20° C. until H$_2$ evolution is ceased, treated with bromochloromethane (13.0 g, 0.10 mol) and treated portionwise with sodium ethoxide (6.0 g, 0.088 mol) over a 5.5 hour period by intermittently cooling to 50° C., adding a portion of sodium ethoxide and heating at reflux temperature. The reaction progress is followed by HPLC analysis. When the reaction is complete, the reaction mixture is concentrated via distillation, diluted with a mixture of methylene chloride and water and treated with a 5% sodium hydroxide solution. The phases are stirred vigorously for 30 minutes and separated. The organic phase is concentrated in vacuo to afford a residue which is recrystallized from hexanes to give the title product as a colorless solid, 8.7 g, mp 91° C. to 92° C. The mother liquors assay for an additional 2.6 g of product to give a total yield of 92.6%.

EXAMPLE 2

Preparation of
4-Chloro-2-(p-chlorophenyl)-1-ethoxymethyl)-5-(trifluoromethyl)pyrrole-3-carbonitrile

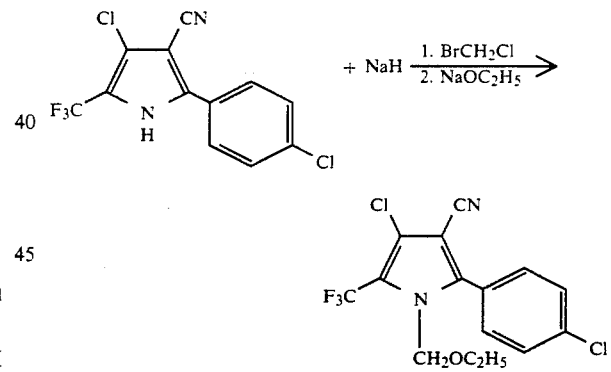

A stirred mixture of a 60% NaH dispersion in mineral oil (1.32 g, 0.0328 mol of NaH) in tetrahydrofuran is treated dropwise with a solution of 4-chloro-2-(p-chlorophenyl)-5-(trifluoromethyl)pyrrole-3-carbonitrile (10.0 g, 0.0328 mol) in tetrahydrofuran at 20° C. to 30° C., stirred for 30 minutes and treated with bromochloromethane (12.72 g, 0.0983 mol) and solid sodium ethoxide (6.7 g, 0.0983 mol). The reaction mixture is heated at reflux temperature for 3 hours, treated with an additional molar equivalent of sodium ethoxide, heated at reflux temperature for another 1.5 hours, cooled to room temperature and diluted with water and ethyl acetate. The organic phase is washed with brine, dried (Na$_2$SO$_4$) and concentrated in vacuo to give a brown oil residue. The residue is purified using basic alumina and toluene and recrystallized from heptane to give the title product as a white solid, 6.5 g (52% yield), mp 100° C. to 103° C.

EXAMPLE 3

Preparation of
4,5-Dichloro-2-(3,4-dichlorophenyl)-1-ethoxymethyl)-pyrrole-3-carbonitrile

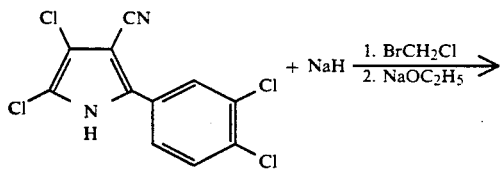

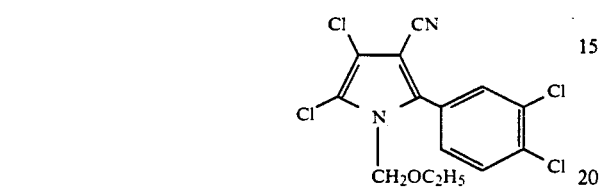

A mixture of a 60% NaH dispersion in mineral oil (1.31 g, 0.0327 mol of NaH) in tetrahydrofuran is treated slowly with a solution of 4,5-dichloro-2-(3,4-dichlorophenyl)pyrrole-3-carbonitrile (10.0 g, 0.0327 mol) in tetrahydrofuran at 20° C. to 30° C., stirred at ambient temperatures for 30 minutes, treated with bromochloromethane (12.7 g, 0.0980 mol) and solid sodium ethoxide (4.4 g, 0.647 mol) and heated at reflux temperature for 2 hours. The reaction mixture is treated with 2 additional molar equivalents of sodium ethoxide over a 2 hour period at reflux temperature, heated at reflux temperature for a further 2 hour period, stirred at room temperature for 16 hours and concentrated in vacuo. The reaction concentrate is diluted with water and ethyl acetate. The organic phase is washed with water and brine, dried (Na$_2$SO$_4$) and concentrated in vacuo to give a residue which is recrystallized from ethyl acetate/heptane to give the title compound as a white solid, 10.6 g (89% yield), mp 126° C. to 130° C.

EXAMPLE 4

Preparation of
2,4,5-Tribromo-1-ethoxymethyl)pyrrole-3-carbonitrile

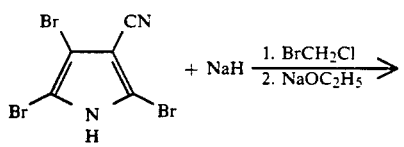

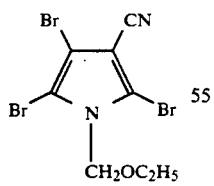

A mixture of a 60% dispersion of NaH in mineral oil (1.22 g, 0.0304 mol NaH) in tetrahydrofuran is treated dropwise with a solution of 2,4,5-tribromopyrrole-3-carbonitrile (10.0 g, 0.0304 mol) in tetrahydrofuran at 20° C. to 30° C. over a 20 minute period, stirred for 30 minutes at ambient temperatures, treated with bromochloromethane (11.80 g, 0.0912 mol) and solid sodium ethoxide (6.2 g, 0.0912 mol), heated at reflux temperature for 4 hours, cooled to room temperature, concentrated in vacuo and diluted with water and ethyl acetate. The organic phase is washed with water and brine, dried (Na$_2$SO$_4$) and concentrated in vacuo to give a residue which is purified by flash chromatography (silica gel; ethyl acetate/heptane) to give the title compound as a white solid, 5.4 g (46.7% yield), mp 139° C. to 143° C.

EXAMPLE 5

Preparation of an alkoxymethyl derivative of an insecticidal pyrrole using dibromomethane

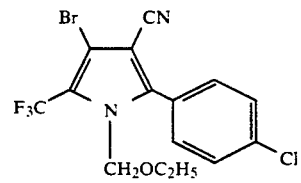

Using essentially the same procedure described in Example 1 and substituting a total of 1.5 molar equivalents of dibromomethane for the bromochloromethane and employing a total of 7.5 molar equivalents of sodium ethoxide, 4-bromo-2-(p-chlorophenyl)-1-ethoxymethyl)-5-(trifluoromethyl)pyrrole-3-carbonitrile is obtained in 85% yield, 11.6 g, identified by HPLC analysis.

EXAMPLE 6

Preparation of an alkoxymethyl derivative of an insecticidal pyrrole using 1.5 molar equivalents of bromochloromethane

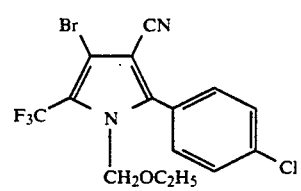

A solution of 4-bromo-2-(p-chlorophenyl)-4-(trifluoromethyl)pyrrole-3-carbonitrile (17.48 g, 0.05 mol) in tetrahydrofuran is added dropwise to a stirred slurry of NaH (60% dispersion in mineral oil, 2.0 g, 0.05 mol NaH) in tetrahydrofuran at 20° C. to 25° C., stirring is continued at room temperature for 15 to 20 minutes, solid sodium ethoxide (5.1 g, 0.075 mol) is added and the resultant mixture is heated to reflux temperature. The resultant refluxing reaction mixture is treated dropwise with a solution of bromochloromethane (9.71 g, 0.075 mol) in tetrahydrofuran over a 3 hour period, heated further at reflux temperature for 1 hour, treated with solid sodium ethoxide (3.4 g, 0.05 mol), continued heating at reflux temperature for an additional 1 hour, treated further with solid sodium hydroxide (1.7 g, 0.025 mol), continued heating at reflux temperature for 16 hours, cooled and concentrated in vacuo. The reaction concentrate is dispersed in water and ethyl acetate. The organic phase is washed with water and brine, dried ($Na_2SO_4$) and concentrated in vacuo to give the title product in 92% purity by glc analysis.

What is claimed is:

1. A process for the preparation of a compound of formula I

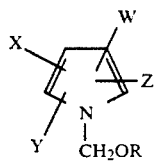

wherein
R is $C_1$–$C_6$ alkyl;
W is CN or $NO_2$;
X is H, CN, halogen or phenyl optionally substituted with one to three halogens, CN, $NO_2$, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, $CF_3$, $R_1CF_2R_2$, $R_3CO$ or $NR_4R_5$ groups;
Y is $CF_3$ or halogen;
Z is H, $CF_3$, halogen or phenyl optionally substituted with one to three halogen, CN, $NO_2$, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, $CF_3$, $R_1CF_2R_2$, $R_3CO$ or $NR_4R_5$ groups;
$R_1$ is H, F, $CHF_2$, CHFCl or $CF_3$;
$R_2$ is $S(O)_n$ or O;
$R_3$ is $C_1$–$C_3$ alkyl, $C_1$–$C_3$ alkoxy or $NR_4R_5$;
$R_4$ is H or $C_1$–$C_3$ alkyl;
$R_5$ is H, $C_1$–$C_3$ alkyl or $R_6CO$;
$R_6$ is H or $C_1$–$C_3$ alkyl and
n is an integer of 0, 1 or 2 which comprises reacting a compound of formula II

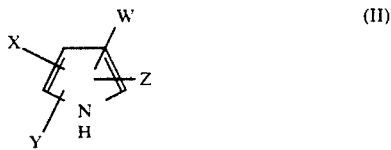

wherein W, X, Y and Z are described above with at least one molar equivalent of a dihalomethane in the presence of at least two molar equivalents of an alkali metal $C_1$–$C_6$alkoxide and optionally about one molar equivalent of an alkali metal hydride and a solvent.

2. The process according to claim 1 wherein the dihalomethane is bromochloromethane, the alkali metal $C_1$–$C_6$alkoxide is sodium ethoxide and the alkali metal hydride is sodium hydride.

3. The process according to claim 1 wherein the dihalomethane is dibromomethane.

4. The process according to claim 1 wherein the solvent is tetrahydrofuran.

5. The process according to claim 1 wherein W is CN or $NO_2$, X is halogen, Y is halogen or $CF_3$ and Z is halogen or phenyl optionally substituted with one or two halogens.

6. The process according to claim 1 wherein W is CN, X is halogen, Y is $CF_3$ and Z is phenyl optionally substituted with one or two halogens.

7. The process according to claim 1 wherein the compound of formula I is 4-bromo-2-(p-chlorophenyl)-1-(ethoxymethyl)-5-(trifluoromethyl)pyrrole-3-carbonitrile.

8. The process according to claim 1 wherein the compound of formula I is 4-chloro-2-(p-chlorophenyl)-1-(ethoxymethyl)-5-(trifluoromethyl)pyrrole-3-carbonitrile.

9. The process according to claim 1 wherein the compound of formula I is 2,4-dichloro-5-(3,4-dichlorophenyl)-1-(ethoxymethyl)pyrrole-3-carbonitrile.

10. The process according to claim 1 wherein the reaction takes place at an elevated temperature.

* * * * *